United States Patent [19]

Schurch

[11] Patent Number: 4,953,389
[45] Date of Patent: Sep. 4, 1990

[54] CAPTIVE BUBBLE SURFACE TENSIOMETER

[75] Inventor: Samuel Schurch, Calgary, Canada

[73] Assignee: University of Calgary, Calgary, Canada

[21] Appl. No.: 422,547

[22] Filed: Oct. 17, 1989

[30] Foreign Application Priority Data

May 2, 1989 [CA] Canada .................................. 599518

[51] Int. Cl.[5] ............................................ G01N 13/02
[52] U.S. Cl. ..................................................... 73/64.4
[58] Field of Search ............................................ 73/64.4

[56] References Cited

U.S. PATENT DOCUMENTS

| | | | |
|---|---|---|---|
| 2,473,553 | 6/1949 | Stokes | 73/64.4 |
| 3,483,737 | 12/1969 | Jennings, Jr. et al. | 73/64.4 |
| 3,990,293 | 11/1976 | Alsop | 73/64.4 |
| 4,523,456 | 6/1985 | Baird et al. | 73/64.4 |

FOREIGN PATENT DOCUMENTS

| | | | |
|---|---|---|---|
| 3441317 | 8/1986 | Fed. Rep. of Germany | 73/64.4 |
| 153229 | 12/1981 | German Democratic Rep. | 73/64.4 |
| 99728 | 6/1983 | Japan | 73/64.4 |
| 987470 | 1/1983 | U.S.S.R. | 73/64.4 |
| 1286949 | 1/1987 | U.S.S.R. | 73/64.4 |

*Primary Examiner*—Hezron E. Williams
*Assistant Examiner*—Joseph W. Roskos
*Attorney, Agent, or Firm*—Albert L. Jeffers

[57] ABSTRACT

A method and an apparatus for determining the surface tension between a gas and a liquid, and wherein the surface tension of a film established on the surface of a bubble in a medium may be calculated. A liquid medium such as an aqueous medium is provided in a chamber. The container is constructed so that an air bubble may be formed in the liquid medium in the chamber and a film of a material, such as a surfactant material, can then be formed at the air-liquid interface. The chamber is also constructed so that the pressure of the liquid medium may be varied. On increasing the pressure of the liquid medium, the bubble volume and its surface area are reduced. Thus, the interfacial film is compressed, and alternatively, when the pressure of the liquid medium is reduced, the film is expanded by the expanding of the bubble. The chamber provides a complete enclosure so that the liquid medium and the surfactant are not exposed to the atmosphere. The surface tension can then be determined on recording the shape of the bubble by way of a computer calculation. Dynamic as well as static surface tension vs area relations can be obtained by adjusting the compression and expansion cycling speed. The invention is especially suitable to study surface active components relating to pulmonary surfactant because the bubble is leak proof and thus mimics the situation in the lung.

42 Claims, 6 Drawing Sheets

CAPTIVE BUBBLE SURFACE TENSIOMETER

BACKGROUND OF THE INVENTION

1. Field of the Invention

The present invention relates to a method and an apparatus for the establishing of the surface tension of the interface between a gas and a liquid medium, and more particularly to a method and apparatus for determining the surface tension of a pulmonary surfactant.

2. Description of the Prior Art

In the past several decades, there has developed a greatly increased understanding of the surfactant system of the lung. Monolayers of lung alveolar surfactant have been shown to develop near zero surface tensions upon dynamic compression in known types of apparatus. The common characteristics of the studies, especially if they are done at 37° C., have involved the requirement of a minimum film compression rate for the surface balance technique or a minimum cycling speed for the pulsating bubble technique. See Goerke, J. and Clements, J. A. (1986); Alveolar surface tension and lung surfactant; In: Handbook of Physiology, Section 3, The Respiratory System. Vol. 111 part 1, edited by A. P. Fishman, P. T. Macklem, J. Mead and S. R. Geiger. Bethesda, Amer. Physiol. Soc. pp 247–261. Although minimum surface tensions below 5 $mN.m^{-1}$ in the film balance or below 1 $mN.m^{-1}$ for the pulsating bubble, can be obtained if the compression rate for pulmonary surfactant films is fast enough, these low surface tensions obtained in vitro have much less stability than the alveolar film in situ.

The stability of the alveolar film in situ has been calculated from lung pressure-volume studies of animal lungs. In lungs held at 40% total lung capacity, the surface tension increased by only 1 to 2 $mN.m^{-1}$ in 20 minutes. See Horie, T. and Hildebrandt, J. (1971); Dynamic compliance, limit cycles, and static equilibria of excised cat lungs. J. Appl. Physiol. 31:423–430. A similar surface tension stability has been obtained by observing the spreading behaviour of fluid droplets placed by micropipets into individual alveolar spaces. See Schurch, S. (1982); Surface tension at low lung volumes: dependence on time and alveolar size. Respir. Physiol. 48:339–355. According to these studies, there is no need for a minimum compression rate of the alveolar film to obtain a near zero and stable surface tension. One inflation-deflation cycle may take between 10 and 30 minutes.

In surface balance experiments, one compression-expansion cycle usually takes 1 to 2 minutes and if the barrier movement is stopped at minimum surface tension, this surface tension may increase in a few minutes to more than 10 $mN.m^{-1}$. For the pulsating bubble method between 10 and 20 cycles per minute are used in order to produce near zero surface tension. However, if cycling is stopped at minimum surface tension, the surface tension increases even more rapidly than in the film balance technique. The reason for this in vitro instability is the relatively large escape route for the film molecules as will be described in more detail below. In the pulsating bubble system, the bubble, which is between 0.8 and 1.1 mm in diameter, is connected to atmospheric air via a plastic tubing of about 0.8 mm in diameter. Only relatively fast cycling can compensate for the film loss up the tubing.

To further describe the above-mentioned bubble system, reference is made to a series of articles by R. E. Pattle, including an article entitled "Maturity of Fetal Lungs Tested by Production of Stable Microbubbles in Amniotic Fluid", British Journal of Obstetrics and Gynecology, August, 1979, Vol. 86, pp 615–622 and "Properties, function, and origin of the alveolar lining layer" (1957). Pattle describes that lung tissue contains surfactant material that stabilize microscopic bubbles suspended in water. He observed such bubbles suspended in a drop of water under a microscope slide. Pattle realized that bubbles trapped under the glass slide contracted and flattened because of the relatively rapid diffusion if he used deaerated water as the suspending medium for the bubbles. It was concluded from the life time of these bubbles that the surface tension of lung extract films must approach zero. Pattle apparently did not realize that use could be made of shape analysis of the deformed bubbles to obtain the surface tension accurately and the corresponding bubble surface areas to construct surface tension vs. area relations.

In a publication entitled "Pulsating bubble technique for evaluating pulmonary surfactant", by Goran Enhorning, there is described a technique of determining surface tension with an apparatus that records pressure across the surface of a bubble, expanded in a sample liquid and communicating with ambient air. Pressure pulsations are described as causing the bubble to expand and contract periodically. From the known pressure gradient across the bubble surface and the bubble radius, the surface tension can be calculated with the law of Laplace. The bubble communicates with the ambient air via a capillary tube, and because the ratio of bubble radius to the tube diameter is relatively small, the surfacted film material has a large escape route. In order to reach near zero surface tension, the bubble has to be compressed at a certain minimum compression rate in order to compensate for the escape of film materials through the tubing. Thus, the method is only suitable for dynamic surface tension measurements because of the film material leakage up the tubing.

In a published articles entitled, "Surface Tension at Low Lung Volumes: Dependence on Time and Alveolar Size" by Samuel Schurch, Respiratory Physiology (1982) 48, 339–335, Elsevier Biomedical Press, "New Insights into Principles of Function and Physiology of Surfactant, Including its Role in Small Airways", by Samuel Schurch, progress in respiratory research, volume 18, pp. 1–9 (1984), there is described technology relating to large captive bubbles whose volumes are controlled by introducing and withdrawing air. The surface tension and bubble areas are determined by shape analysis using established computer approximations. Although the ratio of bubble surface area to tubing diameter is much greater than in the above described design of Enhorning's, there is still film material leakage through air capillary tubing which is used to change the bubble size.

Another described surface tension measuring technique is known as the Langmuir Wilhelmy method, and there are commercially available Langmuir film balance machines sold under the trade mark LAUDA by Sybron/Brinkmann.

The original Langmuir design is described in a text entitled "The Physics and Chemistry of Surfaces" by Neil Kensington Adam, Dover 1968.

The original Langmuir Wilhelmy method was modified by John A. Clements as described in a publication by the Society for Experimental Biology and Medicine, entitled, "Surface Tension and Lung Extracts" by John A. Clements (1957); and a published article entitled "Surface Phenomena in Relation to Pulmonary Function", by John A. Clements, The Physiologist, Vol. 5, 1962; and in a publication entitled "Surface Active Materials from Dog Lung. I. Method of Isolation" by Richard J. King, and John A. Clements, American Journal for Physiology, volume 225 No. 3, September, 1972.

As described in a publication "Time Dependent Changes of the Surface Pressure of Alveolar Surface Layers in the Langmuir Trough" by W. Schoedel et al, Pflugers Arc. 306, pp 20–32 (1969) there is described the use of a rhombic frame to change the film area as a variation of the rectangular trough design of Clements.

A publication entitled "A New Surface Balance for Dynamic Surface Tension Studies" by Boyle and Mautone, Colloids and Surfaces, 4(1982) 77–85, there is described yet another variation of the Langmuir Wilhelmy design.

The above described designs are usable for static and dynamic surface tension vs. area studies.

The Langmuir Wilhelmy method is the one most commonly used in commercially available products. The above described apparatus sold under the trade mark "LAUDA" is a relatively large and expensive machine and is not portable. In this type of machine, there is provided a trough in which the film pressure is measured by a polytetrafluroethylene coated floating barrier. The nature of the operation of the machine necessitates the use of highly trained personnel. The machine, like the apparatus using the pulsating bubble method exhibits in vitro instability which is due to the relatively large escape route for the film molecules. In the surface balance machine, the molecules move up the barrier or escape around the polytetrafluroethylene barrier since the contact surface of the barrier and the water interface is well suited for surfactant spreading.

In the pulsating bubble method, between 10 and 20 cycles per minute are used in order to produce near zero surface tension.

However, if cycling is stopped at minimum surface tension, the surface tension increases even more rapidly than in the Langmuir surface balance apparatus. In the pulsating bubble system, the bubble, between 0.8 and 1.1 mm in diameter, is connected to the atmospheric air via a plastic tubing of about 0.8 mm in diameter. Only relatively fast cycling can compensate for the film loss up the tubing.

SUMMARY OF THE INVENTION

It is an object of the present invention to provide a simple apparatus for testing the surface tension at the interface of a bubble contained within a liquid medium.

More specifically, it is an object of the present invention to provide a method of determining the surface tension of a lung surfactant film in an arrangement which more closely approximates the situation in the lung.

According to one aspect of the present invention, there is provided a method of determining the interface tension between a gas and a liquid, the method including the steps of providing a liquid medium in a chamber and injecting a bubble of the gas into the liquid medium. The method further includes the steps of increasing and decreasing the pressure of the liquid medium within the chamber to reduce and expand the bubble, and determining the surface tension of the gas-liquid interface from the shape of the bubble.

Another aspect of the invention resides in an apparatus in a form of a captive bubble surface tensiometer which has a chamber for containing a liquid medium therein and means for forming a gas bubble in the liquid medium and having a gas-liquid interface with the liquid medium. The apparatus includes means for controlling the pressure of the liquid medium to compress and expand the bubble. Means is provided for determining the surface tension of the gas liquid interface from the shape of the gas bubble.

More specifically, the method of the present invention includes the step of forming a surfactant film at the interface and wherein the surface tension of the surfactant film is determined.

The present invention is directed toward mimicking the surface tension characteristics of the alveolar film in situ and to provide a new, more sensitive test system to investigate fetal lung maturity and to study the surface activity in bronchial-alveolar lavage fluid from patients with lung diseases. Accordingly, it is the purpose of the present invention to develop a test system in the form of a diagnostic tool, not only to assess the fetal lung maturity, but also to assess or improve the diagnosis of various diseases of the mature lung.

In the specific examples of the invention disclosed herein, an air bubble is formed inside an aqueous medium in a chamber below a hydrophilic surface, such as an agar gel or an inert metal. The surfactant film is formed at the air-liquid interface of the bubble either by absorption of surfactant material from the aqueous medium or by spreading the material at the interface with a syringe. The bubble area is reduced in order to compress the interfacial film by applying pressure to the liquid medium. Likewise the film is expanded by expanding the bubble by lowering the pressure in the chamber. The bubble has no communication with the outside air, and the bubble surfaces are interfaces between an aqueous medium and air and between a material totally wettable by water and air. The surface tension and area of the bubble are determined from the bubble shape by computer approximation.

Dynamic as well as static surface tension-area relations can be obtained by adjusting the compression-expansion cycling speed.

The device is specially suitable to study surface active components relating to pulmonary surfactant because the bubble is leak proof and thus mimics the situation in the lung. In the lung of a human adult, more than 100 square meters of surface area is connected to the trachea with its perimeter of about 10 cm. Thus, a very large surface area drains into a few major bronchi, and finally into the trachea, minimizing the escape of the alveolar film molecules.

As will be apparent from the description below, the apparatus of the present invention is inexpensive to produce and is portable. In view of the simple nature of operation, no significant training is required for carrying out a test on the apparatus of the present invention.

The apparatus of the present invention has been found to be more sensitive for measuring the quality of lung surfactant fluid because the system permits measurement of near zero surface tension.

BRIEF DESCRIPTION OF THE DRAWINGS

In the accompanying drawings, which illustrate examples and characteristics of the present invention.

DESCRIPTION OF PREFERRED EMBODIMENTS

Figure 1:
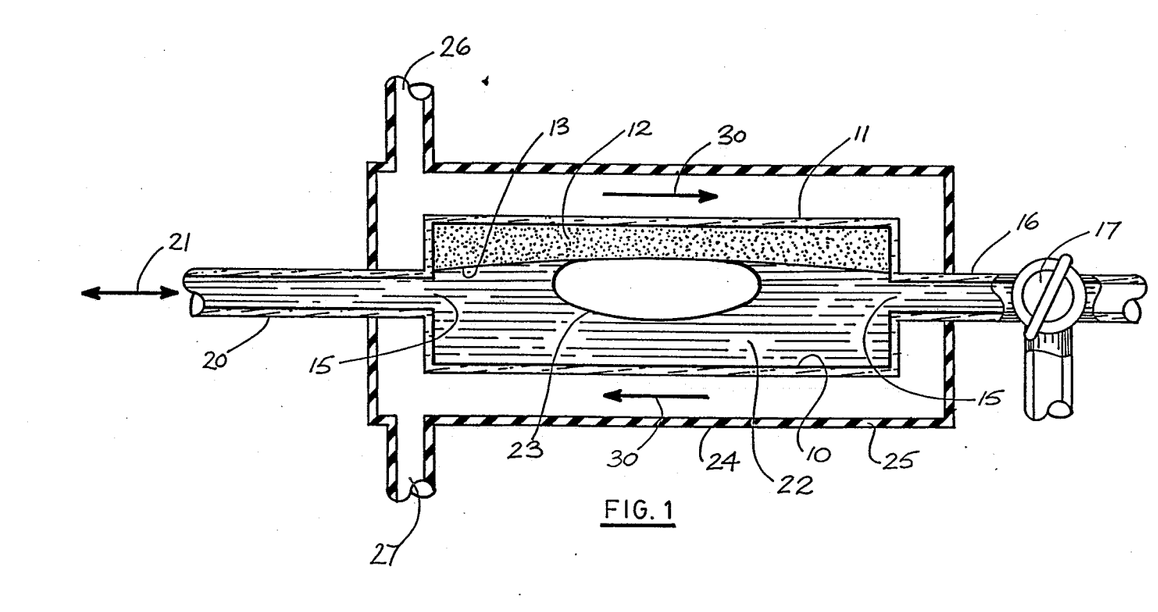
FIG. 1 is a cross sectional view through a simple form of the present invention.

In FIG. 1, reference character 10 denotes a chamber formed by a cell 10 which may be in the form of a glass, flow-through cell. An example of the volume of the cell is 2 ml. In the upper portion of the chamber, there is provided a layer 12 of a hydrophilic material, such as agar gel, or as will be explained in more detail below, the layer may be of a hydrophobic material, depending on the liquid medium utilized. The lower surface 13 of the layer is of slight concave configuration. The cell 11 has openings 14 and 15 at opposite ends thereof, the opening 14 being connected to a conduit 16 provided with a stopcock 17. The opening 15 is connected via conduit 20 to means (not shown) for controlling the medium pressure within the chamber. The pressure may be raised and lowered as indicated by the arrow 21. The apparatus as shown in FIG. 1 includes an outer housing 24 which surrounds the cell 11 and is spaced therefrom so as to define an outer fluid jacket 25 which has an inlet 26 and an outlet 27. Means is provided for supplying a temperature controlled fluid, such as water, into inlet 26, and the fluid circulates through the jacket from inlet 26 to outlet 27 as indicated by the arrows 30 to thereby maintain the liquid medium in the chamber at a fixed temperature.

The chamber 10 may be filled through stopcock 17 with a liquid medium 22. The medium, which may be an aqueous suspension of lung surfactant extract, is fed to the interior of the cell 11 through conduit 16. A captive bubble 23, which in its original size is about two to three ml. in diameter, may be formed by a syringe in the surfactant solution. Stopcock 17 is closed and the size of the bubble is expanded to about six to seven ml in diameter by lowering the pressure in the chamber 11 by way of the pressure control means (not shown). During absorption of surfactant onto the bubble surface, the bubble 23 assumes the shape illustrated in FIG. 1 indicating decreasing surface tension. Increased pressure causes the bubble to shrink, and as the surface tension decreases, the bubble flattens.

As indicated, the pressure is increased in order to decrease the bubble surface to compress the surfactant film. As the surfactant film is compressed progressively, the surface tension falls toward a possible minimum value.

Figure 4A:
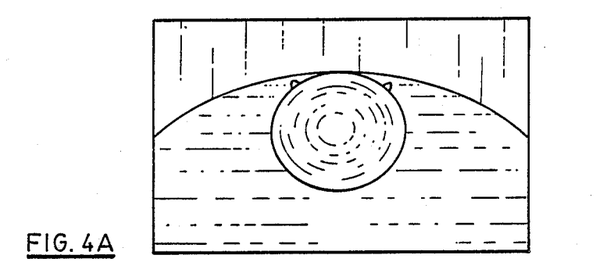
FIGS. 4A–4D illustrate the shape of the captive bubble in the medium within the chamber during different stages.

FIGS. 4A–4D depict pictures of the bubble taken in four different stages in a lung surfactant solution of a concentration of 50 ug/ml of phospholipids in a salt solution, as follows:

4(A) Initial bubble of atmospheric air, picture taken prior to surfactant absorption. Surface tension=69.8 $mN.m^{-1}$; Bubble area=0.37 $cm^2$.

Figure 4B:
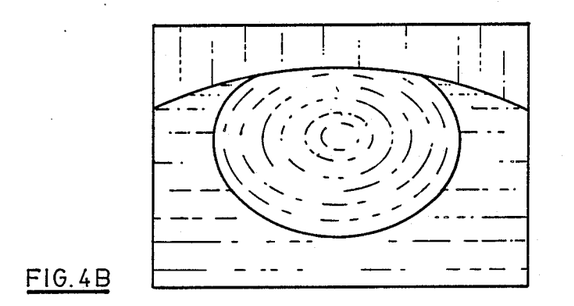

4(B) The bubble in the expanded state prior to substantial surfactant absorption at the time taken as zero regarding the absorption process. The bubble was expanded by lowering the chamber pressure to approximately 0.1 atm by moving slightly back the piston of the gastight syringe. Surface tension=68.4 $mN.m^{-1}$; Bubble area=0.91 $cm^2$.

Figure 4C:
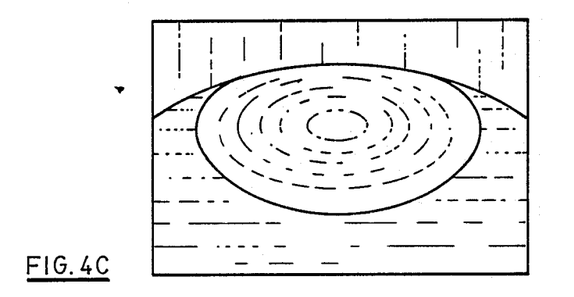

4(C) The bubble after surfactant absorption for 5 min. at 37° C. Surface tension=32.0 $mN.m^{-1}$; Bubble area=0.98 $cm^2$.

Figure 4D:
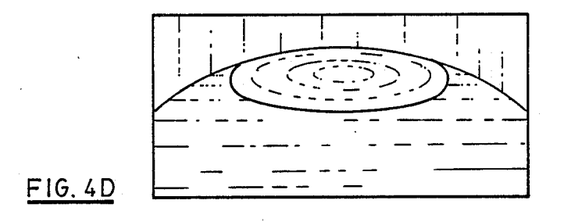

4(D) The bubble after increasing the chamber pressure to slightly above atmospheric. This causes the bubble area to shrink, and the surfactant film at the bubble surface to lower its surface tension. Surface tension=2.6 $mN.m^{-1}$; Bubble area=0.56 $cm^2$.

Figure 5:
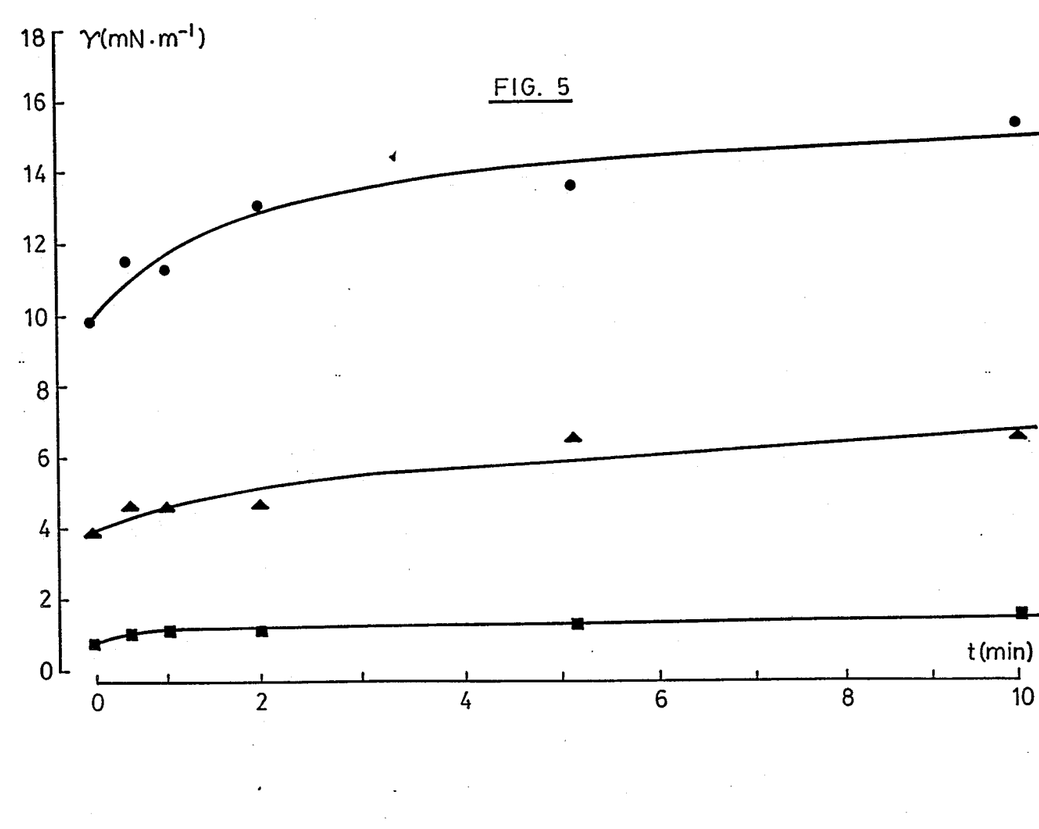
FIG. 5 is a line graph showing the surface tension for the surfactant versus time.

Referring to FIG. 5, there is illustrated surface tension versus time relations. The top line in the graph illustrates, for example, the relationship after two compressions. The middle line illustrates the same condition, but after five consecutive compressions. The bottom line is again under the same conditions after ten to fifteen consecutive compressions.

Again, the error bars indicate standard for four independent experiments.

Figure 6:
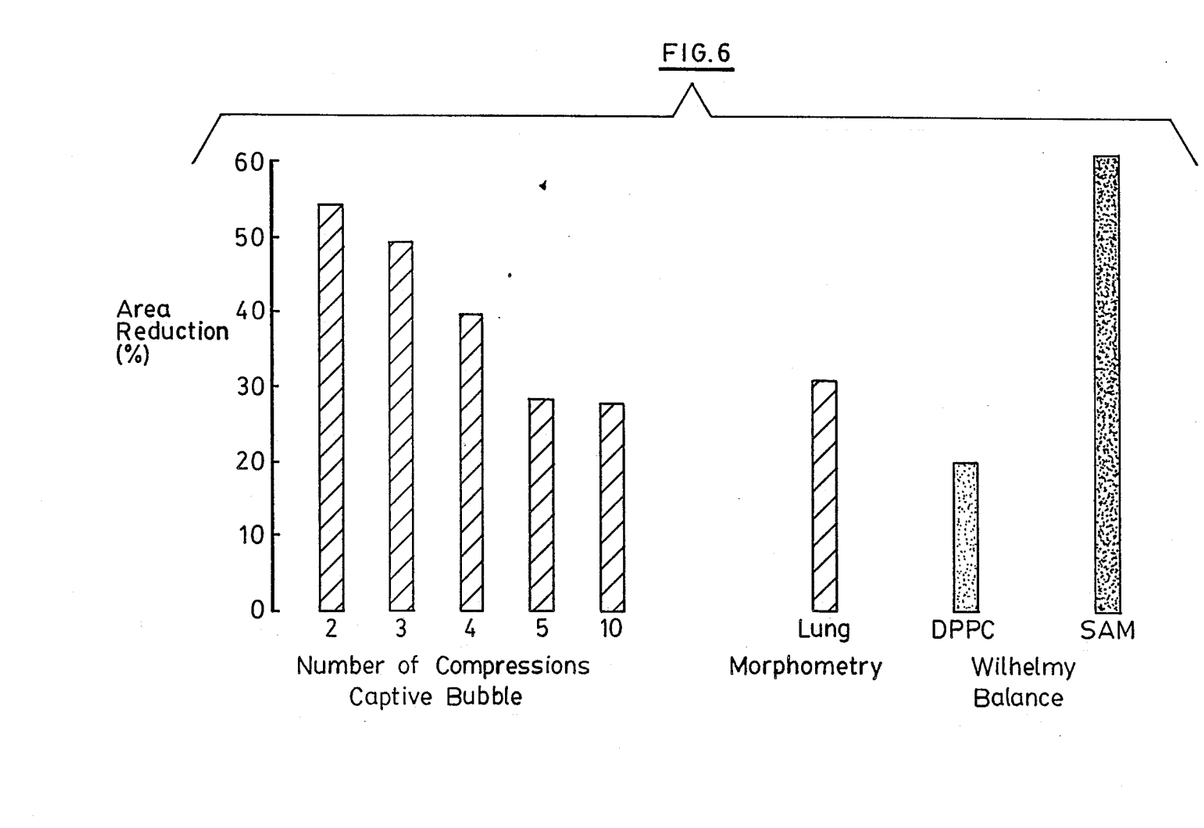
FIG. 6 is a bar graph illustrating the area reduction needed for the surface tension of the surfactant film to fall from 30 to less than 2 $mN.m^{-1}$.

The area reduction needed for the surface tension to fall from 30 to less than 2 $mN.m^{-1}$ decreases more than 50% after two film compressions to less than 30% after ten compressions for lipid extraction surfactant. As a comparison, in the lung, the alveolar area decreases about 30% for the surface tension interval from 30 to less than 2 $mN.m^{-1}$. See Bachofen et al., Relations among alveolar surface tension, surface area, volume, and recoil pressure, T. Applied Physiol. 62: 1878–1887, 1987. For a pure DDPC monolayer, only about 20% area reduction is needed for the same surface tension interval. For natural surface active material (SAM) for the first compression cycle in the above-described Langmuir film balance system, more than 60% area reduction is needed for the surface tension to decrease from 30 to about 10 $mN.m^{-1}$. See Goerke, J. and Clements, J. A. (1986); Alveolar surface tension and lung surfactant; In: Handbook of Physiology, Section 3, The Respiratory System. Vol. 111, part 1, edited by A. P. Fishman, P. T. Macklem, J. Mead and S. R. Geiger. Bethesda, Amer. Physiol. Soc. pp 247–261.

As an alternative to the above described method of achieving the surfactant absorption, droplets of surfactant solution may be spread via syringe onto the bubble surface. It should also be realized that in place of the above described cell, it is possible to use disposable plastic cuvettes for the sample chamber. The chamber may be oriented vertically instead of horizontally as shown in FIG. 1 depending on the position of the hydrophilic sealing or upper layer for the captive bubble.

It is preferable that the lower surface of the hydrophilic layer which forms a ceiling of the chamber should be slightly concave as illustrated in FIG. 1 in order to stabilize the bubble position and to prevent the bubble from contacting the chamber walls.

With respect to the manner of achieving a variation in pressure for the liquid medium, the sample chamber may be connected to a five ml Hamilton gas type syringe. Movement of the piston or plunger into and out of the syringe may be controlled by the feed system consisting of a threaded shaft, and a pressure gauge may be added to the liquid circuit for easier control of the bubble size between maximum and minimum surface area or volume.

In the example which has been described, wherein an air bubble is formed in water and there is provided a surfactant zone layer, the hydrophylic layer functions well because the bubble will then have a constant angle close to 180° and the bubble with its interface functions as a closed system insofar as surface leakage is concerned. If, on the other hand, the top surface is formed of plastic material, the air bubble with the surfactant layer would adhere to the plastic forming a constant angle smaller than 180°. In any event, even in the latter case the surface tension could still be determined by using established approximations.

Because the agar gel is slightly concave, it helps in centering of the bubble which is exceedingly difficult to do if the surface is completely flat. Agar gel has been chosen because it is easy to mold into the required slightly concave shape. In the case of a surfactant acting at an air-water interface, a hydrophylic substance such as an agar gel or any other hydrophylic gel, or for that matter, any other hydrophylic substance would work well as a support for the air bubble with its surfactant film. The concentration of the agar must be sufficient to provide mechanical stability. Thus, the minimum agar concentration should be approximately 0.5% w/w in water. The maximum concentration should not exceed 2% because the gel should contain enough water to keep the agar ceiling hydrophilic. The agar layer may be replaced by a relatively inert metal such as stainless steel, but gold or platinum could also be used.

In referring to an aqueous medium, this is meant to include hydrophilic liquids other than water, such as ethanol, other alcohols, or possibly dimethyl sulfoxide (DMSO). In addition to the use of a hydrophilic sealing, of agar gel, an inert metal can be used. The liquid medium used need not be aqueous, but it may be an oil, such as an alkane. If such an alternative is used, the layer 12 must be made of a hydrophobic material. The layer may be molded from materials, including paraffin, polyethylene or other plastic materials so as to guarantee wetting by the liquid phase. Another feasible material is polytetrafluroethylene, which is sold under the trade mark "TEFLON".

EXAMPLE I

A lipid extract of bovine pulmonary surfactant was suspended in saline which contained 1 mM CaCl2, and was filled into a plastic sample cup. The final concentration of the lipid extract in the chamber was 1.2 mg/ml. A bubble of atmospheric air, 2 to 3 mm, in diameter was formed inside the chamber by using a Hamilton microliter syringe. A second Hamilton syringe of the gastight type, and provided with a threaded shaft, was filled with saline and connected via a polyethylene tubing and a stopcock to the sample chamber. Except for the captive bubble, all additional air bubbles were squeezed out of the system.

The pressure in the chamber was then reduced to approximately 0.1 atm. which caused the bubble to double its original size to 4 to 6 mm in diameter. At this point, timing for the surfactant absorption was started as was a video recording through a Wild M 420 Makroskop. After the standard absorption time of 5 minutes at 37° C., the surface tension was between 25 and 30 $mN.m^{-1}$. The pressure in the chamber was then increased stepwise by turning the shaft 5 to 10 degrees for each step. After each step, 2 to 5 seconds were allowed for equilibrium to be established. As the pressure increased, the bubble surface decreased, compressing the surfactant film around the captive bubble which flattened progressively, indicating decreasing surface tension. At a certain point, the bubble suddenly changed its shape from flat to more round, indicating a sudden increase in surface tension. The pressure of the liquid medium was then lowered and the bubble size was restored. A second compression-expansion cycle was then restarted. With increasing numbers of cycles, the minimum surface tension decreased and became more stable.

It is apparent from the above that with the apparatus of the present invention, small samples of lung surfactant can be used, and due to the closed system, the surfactant is less apt to be contaminated.

Figure 2:
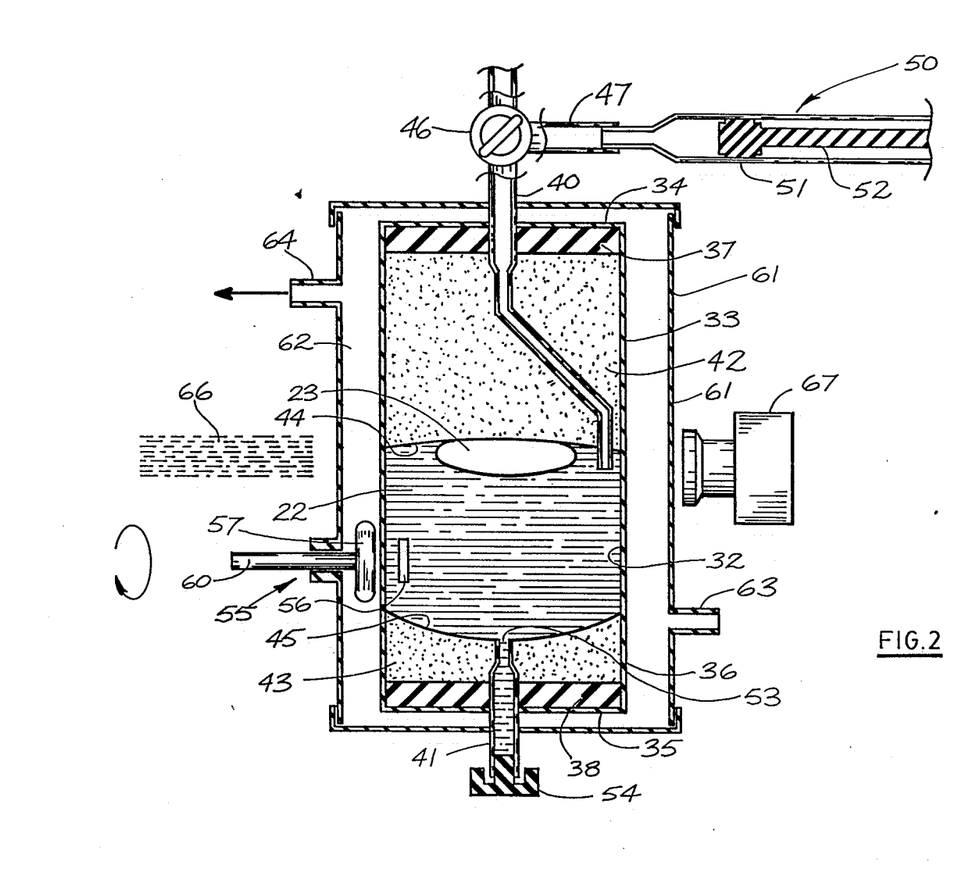
FIG. 2 is a cross sectional view through an alternative structure of the present invention.

Turning now to the alternative embodiment shown in FIG. 2, it is to be appreciated that the principle of operation with this apparatus is the same as that described above. Chamber 32 is contained within an inner container 33 having top and bottom walls 34 and 35, respectively, and a surrounding side wall 36. The container may be in the form of a Lucite cuvette. Additional plastic layers 37 and 38 may be provided adjacent the top and bottom walls 34 and 35 respectively to reinforce the relatively thin walls and to hold the conduits 40 and 41 rigidly in place. Below the layer 37 there is provided a hydrophylic layer 42, which, as indicated above, may be a agar gel. Above the plastic layer 38 a bottom hydrophylic layer 43 is also provided. The hydrophylic layer 42 has a slightly concave lower surface 44 providing a ceiling for the chamber 32. The lower hydrophylic layer 43 has a more prominent concave upper surface 45. Again, if the liquid medium to be used in the chamber is oil, then the layers 42 and 43 should be formed of a hydrophobic material.

As shown in FIG. 2, the conduit 40 passes through the top of the inner container 33 and passes through the plastic layer 37 as well as through the layer 42, thus providing an internal passage to the chamber 32. The conduit 40 is provided with a stopcock 46 adapted to place an input conduit 47 in communication with the conduit 48. The input conduit 47 is adapted to receive the output end of a Hamilton gastight syringe 50. The Hamilton syringe 50 is provided with a barrel 51 and a piston or plunger 52. The movement of the plunger 52 may be controlled by a threaded shaft as will be described in more detail in connection with the embodiment shown in FIG. 3. The aqueous medium 22 may be injected into the chamber 32 in a manner described in connection with the embodiment of FIG. 1.

A medium passage, which is provided by conduit 41 communicates with a centrally disposed internal port 53 in the concave surface 45 of the lower layer 43. The outer end of the conduit 41 is provided with a closure means or cap 54. The bubble 23 may be formed in the aqueous medium 22 by way of a needle connected to a syringe, or the bubble may be formed directly by sucking air into the liquid filled chamber through conduit 41, by simply lowering the pressure of the liquid medium. It can be seen that the bubble may also be formed in the chamber by turning the device upside down and by then inserting the aqueous medium which may contain the surfactant solution, by way of the internal passage controlled by the stop cock. The aqueous medium is filled into the air containing chamber until only a small bubble of the desired size is left. By then turning the chamber right side up, the bubble floats up toward the hydrophylic ceiling provided by lower concave surface 44. After squeezing out the undesired air in the bottom of conduit 42, the conduit is closed by the cap 54.

It might be noted that the upper concave surface 45 of the lower layer 43 is also useful in getting rid of unwanted air bubbles which frequently exists in the medium in the chamber. When the device is turned upside down, the concave shape of the surface 45 assists in directing or clustering the unwanted bubbles near the centre of the concave surface so that they may be evacuated through the port 53.

It should be noted that the liquid or the surfactant suspension may be either introduced through the Hamilton gastight syringe 50 on top or the liquid medium may be drawn into the chamber through the bottom opening while the cap 54 is removed. The testing bubble 23 is most easily formed by drawing a small amount of air into the chamber from the bottom. In order to fill the air lines with fluid medium, the chamber is turned upside down and tilted slightly so that the testing bubble moves into a corner of the chamber. By applying fluid with the Hamilton gastight syringe, the chamber is totally filled with the liquid medium, except for the testing bubble, and the chamber is locked. The chamber is then turned right side up and the testing bubble floats into the centered position in the middle of the upper agar bed. The pressure in the chamber is then varied by moving liquid in or out of the chamber, using the Hamilton gastight syringe.

The operation of the device shown in FIG. 2, may be improved by utilizing a stirring device as denoted by reference character 55. The stirring device includes an internal magnetic stirrer 56, located immediately adjacent the side wall of the container 33. The magnetic stirrer is in the form of a ferro-magnetic member as is a magnetic drive member 57 located immediately outside of the side wall 36 adjacent the magnetic stirrer 56. The magnetic drive member is mounted at the end of a shaft 60 arranged to be rotated by a drive means (not shown), thus, activation of the drive means rotates magnetic drive member 57 which in effect is magnetically connected to the magnetic stirrer so that the magnetic stirrer rotates with the drive means and therefore circulates the aqueous medium within the chamber 32.

An external housing 61 surrounds and is spaced from the inner container 33, so as to provide a fluid jacket 62 having inlet and outlet ports 63 and 64, respectively. Thus, fluid such as air maintained at 37° C. may be passed through the jacket to maintain the surfactant at a fixed temperature. The outer housing may be in the form of a Lucite box. The drive shaft 60 is journalled in a bearing means 65 provided in the housing so as to enable the mounting of the magnetic drive member immediately adjacent the side of the container 33. A light source 66 may be aligned with the location of the bubble as set by the upper concave surface 44. Thus, the light is directed through the bubble and is received by a CCD camera 67 located on the opposite side of the housing 61. As indicated above, the surface tension is calculated by way of a computer program developed to interpret the shape of the bubble as transmitted into the camera pickup.

The video picture of a bubble taken with the video copier are digitized and the surface tension, surface area and bubble volume (if desired) are calculated with a computer program based on the formulae of Rotenberg et al (1983) J. Colloid and Interface Sci. 93:169–183. However, bubble surface tensions can be calculated by a more simple procedure described by Malcolm and Elliott (1980) Canadian J. Chem. Engin. 58:151–152. These authors use a fourth degree polynomial approximation for sessile drops and captive bubbles having a 180° contact angle. Only the total bubble height and the bubble diameter are needed. For flat bubble an even simpler formula, again described by Malcom and Elliott, can be used: $\gamma = \Delta \rho g \cdot H^2 / 4$ where $\Delta \rho$ is the density difference between air and the aqueous medium, g is the acceleration due to gravity, and H is the greatest height from bottom to top of the bubble. Since in the latter two methods, the bubble surface area is not given, the areas are calculated by digitizing the bubble contour and using straight forward computer approximation.

Figure 3:
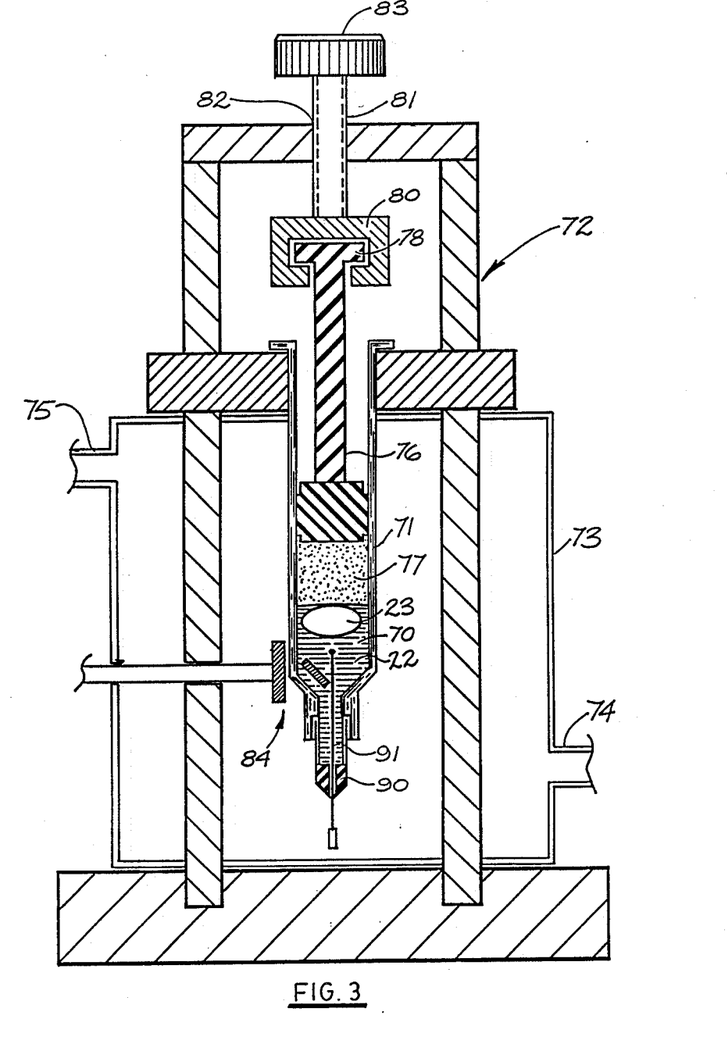
FIG. 3 is a cross sectional view through yet a further alternative construction of the invention.

In the embodiment shown in FIG. 3, the chamber 70 is formed within a glass barrel 71. The glass barrel is mounted within a frame work 72 and is surrounded by a housing 73 having an inlet 74 and an outlet 75, so that a temperature controlled fluid can be circulated around the glass barrel. A piston or plunger 76 extends downwardly through the open upper end of the barrel 71. Below the plunger 76 there is provided a hydrophylic or a hydrophobic layer 77, depending on whether an aqueous or an oil medium is to be used. The liquid medium 22 and the bubble 23 may be drawn into the glass barrel by removing a cap 90, which contains a thermistor probe 91 at the bottom of the glass barrel, and then moving the plunger 76 upwardly. The upper end of the plunger 76 is provided with the enlarged portion 78 received within the clamp portion 80 carried by the threaded shaft 81. The threaded shaft 81 is threaded into a threaded opening 82 in the frame work 72. A threaded shaft 81 is provided with a knurled wheel portion 83 so that the shaft 81 may be readily turned by finger operation of the knurled wheel 83. Thus, the plunger may be pushed into or withdrawn relative to the chamber 70 so as to achieve the compression and the expansion of the bubble.

The device shown in FIG. 3 is provided with a magnetic stirring device 84 of a structure similar to that shown in the embodiment of FIG. 2.

Numerous variations to the above described embodiments but which are within the spirit of the present invention as defined in the claims will be obvious to those skilled in the art.

What I claim is:

1. A method of determining the interface tension between a gas and a liquid comprising the steps of providing a liquid medium in a chamber, injecting a bubble of the gas into the liquid medium, increasing and decreasing the pressure of the liquid medium within the chamber to reduce and expand said bubble, and determining the surface tension of the gas-liquid interface from the shape of said bubble.

2. A method as defined in claim 1, and further including the further step of forming a surfactant film at said interface, and wherein the surface tension being determined is that of the surfactant.

3. A method as defined in claim 1 or 2, wherein said liquid medium is aqueous and said bubble is air.

4. A captive bubble surface tensiometer comprising a chamber for containing a liquid medium therein means for forming a gas bubble in said liquid medium and having a gas-liquid interface with said liquid medium,
means for controlling pressure of said liquid medium to compress said bubble and expand said bubble, and means for determining the surface tension of the gas-liquid interface from the shape of the air bubble.

5. A captive bubble surface tensiometer comprising:

a chamber for containing a liquid medium in said chamber, means for forming an air bubble in said medium and having air liquid interface with said liquid medium, means for forming a surfactant film at said air-liquid interface, means for controlling pressure of said medium to alternately reduce and expand said air bubble and thereby compress and expand said surfactant film, and means for determining the surface tension from the shape of the air bubble.

6. A tensiometer as defined in claim 5 wherein said liquid medium is an aqueous medium.

7. A tensiometer as defined in claim 6 and including an upper layer of hydrophilic material in said cell and forming an upper surface of said chamber.

8. A tensiometer as defined in claim 6, wherein said chamber is formed by an inner container having top and bottom walls and a surrounding side wall, at least the side wall being of transparent material.

9. A tensiometer as defined in claim 8, wherein said chamber is defined between an upper hydrophilic layer and a lower hydrophilic layer.

10. A tensiometer as defined in claim 9, wherein said layers have surfaces of slightly concave configuration facing said chamber.

11. A tensiometer as defined in claim 10, wherein an opening is provided in the slightly concaved surface of the lower layer, and further comprising a passage communicating said opening to an external port, and means for closing the external port.

12. A tensiometer as defined in claim 8, wherein said hydrophilic layers are formed by agar gel.

13. A tensiometer as defined in claim 8, and including an internal conduit extending from an exterior stop clock to within said chamber.

14. A tensiometer as defined in claim 13, wherein said stop clock is adapted to place a supply conduit in communication with said internal conduit.

15. A tensiometer as defined in claim 14, wherein a hamilton gas tight syringe communicates with said supply conduit.

16. A tensiometer as defined in claim 8 and further including a housing spaced from and enclosing said inner container, a fluid jacket being defined between said inner container and said housing inlet and outlet means in communication with said jacket, and means for providing a temperature controlled fluid to said inlet means.

17. A tensiometer as defined in claim 16 including means for stabilizing said bubble in a set location within said chamber.

18. A tensiometer as defined in claim 17, wherein said means for stabilizing said bubble in a set location includes an upper surface of slightly concave shape in said inner container.

19. A tensiometer as defined in claim 18, and including an upper layer of hydrophilic material forming said upper surface.

20. A tensiometer as defined in claim 19, wherein at least the side wall of said inner container and said housing are formed of transparent material.

21. A tensiometer as defined in claim 20, wherein said transparent material is Lucite.

22. A tensiometer as defined in claim 21 and further comprising a light source outside of said housing and at one side of said set location, said light source being aligned with said set location, and a camera pick up outside of and at the opposite side of the outer container for receiving light passing through said set location from said light source.

23. A tensiometer as defined in claim 8 and further comprising a magnetic stir means including a stirring member of ferromagnetic material within said chamber and a ferromagnetic drive member positioned immediately adjacent to but outside of said container side wall, and means for rotating said drive member to cause rotation of said stirring member within said chamber.

24. A tensiometer as defined in claim 5 wherein the liquid medium is an oil medium.

25. A tensiometer as defined in claim 24, wherein said upper layer is a agar gel.

26. A tensiometer as defined in claim 24, and including an upper layer of hydrophobic material and forming an upper surface of said chamber.

27. A tensiometer as defined in claim 26, wherein said upper layer of hydrophobic material is formed by paraffin, polytetrafluroethylene, or of polyethylene or other plastic material.

28. A tensiometer as defined in claim 7 or 26, wherein said layer has a slightly concaved lower surface.

29. A tensiometer as defined in claim 24, wherein said chamber is formed by an inner container having top and bottom walls and a surrounding side wall, at least the side wall being of transparent material, the chamber being defined between upper and lower layers of hydrophobic material.

30. A tensiometer as defined in claim 29, wherein said layers are formed of paraffin, polytetrafluroethylene or other plastic material.

31. A tensiometer as defined in claim 24, wherein said chamber is formed by an inner container having top and bottom walls and a surrounding side wall, and further including a housing spaced from and enclosing said inner container, a fluid jacket being defined between said inner container and said housing inlet and outlet means in communication with said jacket, means for providing a temperature controlled fluid to said inlet means, means for stabilizing said bubble in a set location within said chamber including an upper surface of slightly concave shape in said inner container, said upper surface being defined by the upper layer of hydrophobic material.

32. A tensiometer as defined in claim 31, wherein said open end of said barrel is upperly open and said plunger extends downwardly into said barrel, said chamber being formed between an upper layer and a lower end of said barrel, a lower end of said plunger engaging said layer for movement of said plunger downwardly to compress the medium and upwardly to reduce the pressure in said medium.

33. A tensiometer as defined in claim 32, wherein liquid medium is an aqueous medium, and said upper layer is a hydrophilic material.

34. A tensiometer as defined in claim 32, wherein said liquid medium is an oil medium, and said upper layer is a hydrophobic material.

35. A tensiometer as defined in claim 32, 33 or 34 wherein a lower surface of said layer has a slightly concave surface for stabilizing the location of said bubble.

36. A tensiometer as defined in claim 5, wherein said chamber is formed by a cell of at least partially transparent material.

37. A tensiometer as defined in claim 36, wherein the cell has openings at opposite ends, one opening being in communication with a conduit having a stop cock, and the other being in communication with the means for controlling said medium pressure.

38. A tensiometer as defined in claim 37, and including an outer housing surrounding said cell and spaced therefrom for defining an outer fluid jacket enclosing said cell, and means for forcing a flow of fluid through said jacket for maintaining said medium at a fixed temperature.

39. A tensiometer as defined in claim 37, wherein said cell is a glass flow-through cell.

40. A tensiometer as defined in claim 5, and including a transparent barrel mounted within a framework and having an open end, a plunger extending into the barrel and forming said chamber therewith, and means for selectively driving said plunger further into said barrel to cause compression in said chamber or to withdraw said plunger to reduce said pressure within said chamber.

41. A tensiometer as defined in claim 40 and including a framework supporting said barrel, and a threaded shaft received in a threaded opening in said framework and engaging said plunger whereby turning of said threaded shaft in opposite directions causes said plunger to feed into and out of said barrel.

42. A tensiometer as defined in claim 41, 32 or 33, wherein said framework includes a box surrounding said barrel and defining a fluid chamber inclosing said barrel, said fluid chamber having means for receiving a temperature controlled fluid for maintaining the medium at a constant preselected temperature.

* * * * *